United States Patent
Aqad et al.

(10) Patent No.: US 9,720,321 B2
(45) Date of Patent: Aug. 1, 2017

(54) LACTONE PHOTOACID GENERATORS AND RESINS AND PHOTORESISTS COMPRISING SAME

(75) Inventors: Emad Aqad, Northborough, MA (US); Mingqi Li, Shrewsbury, MA (US); Cheng-Bai Xu, Southboro, MA (US); Cong Liu, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/297,031

(22) Filed: Nov. 15, 2011

(65) Prior Publication Data

US 2012/0129104 A1 May 24, 2012

Related U.S. Application Data

(60) Provisional application No. 61/458,015, filed on Nov. 15, 2010.

(51) Int. Cl.
*G03F 7/004* (2006.01)
*C07D 493/08* (2006.01)
*G03F 7/039* (2006.01)

(52) U.S. Cl.
CPC ......... *G03F 7/0045* (2013.01); *C07D 493/08* (2013.01); *G03F 7/0046* (2013.01); *G03F 7/0397* (2013.01)

(58) Field of Classification Search
None
See application file for complete search history.

(56) References Cited

U.S. PATENT DOCUMENTS

| | | | |
|---|---|---|---|
| 7,304,175 B2 | 12/2007 | Harada et al. | |
| 2007/0027336 A1 | 2/2007 | Yoshida et al. | |
| 2008/0081293 A1* | 4/2008 | Harada et al. | 430/287.1 |
| 2008/0085469 A1 | 4/2008 | Ohsawa et al. | |
| 2010/0099042 A1 | 4/2010 | Ohashi et al. | |
| 2010/0136479 A1 | 6/2010 | Yamaguchi et al. | |
| 2011/0250538 A1 | 10/2011 | Li et al. | |
| 2012/0015299 A1 | 1/2012 | Komuro et al. | |
| 2012/0107744 A1 | 5/2012 | Utsumi et al. | |

FOREIGN PATENT DOCUMENTS

| | | | |
|---|---|---|---|
| JP | 2008268744 A | * | 11/2008 |
| JP | 2010039146 A | * | 2/2010 |

OTHER PUBLICATIONS

Machine translation JP 2008-268744. Nov. 6, 2008.*
Machine translation JP 2010-039146. Feb. 18, 2010.*
European Search Report of corresponding European Application No. 11 18 9110.
English Language Summary of Notification of Reason for Refusal for Japanese Patent Application No. 2011-249145, Dispatch Date: Jul. 16, 2015 (3 Pages).
English Language Summary of Fifth Office Action of counterpart Chinese Patent Application No. 20110462560.5 (2 Pages).
English Language Summary of First Office Action of counterpart Chinese Patent Application No. 20110462560.5 (2 Pages).

* cited by examiner

*Primary Examiner* — Cynthia H Kelly
*Assistant Examiner* — Alyssa L Cepluch
(74) *Attorney, Agent, or Firm* — Mintz Levin Cohn Ferris Glovsky and Popeo, P.C.; Peter F. Corless

(57) ABSTRACT

New lactone-containing photoacid generator compounds ("PAGs") and photoresist compositions that comprise each PAG compounds are provided. These photoresist compositions are useful in the manufacture of electronic device.

9 Claims, No Drawings

LACTONE PHOTOACID GENERATORS AND RESINS AND PHOTORESISTS COMPRISING SAME

This application claims the benefit of priority under 35 U.S.C. §119(3) to U.S. Provisional Application No. 61/458,015, filed on Nov. 15, 2010, the entire contents of which are incorporated by reference.

This invention relates to new lactone monomers. In particular, the invention relates to lactone-containing photoacid generator compounds ("PAGs") and photoresist compositions that comprise such PAG compounds. Additionally, the invention relates to resins that contain a lactone repeat unit and photoresist compositions that comprise such lactone resins.

Photoresists are photosensitive films for transfer of images to a substrate. They form negative or positive images. After coating a photoresist on a substrate, the coating is exposed through a patterned photomask to a source of activating energy, such as ultraviolet light, to form a latent image in the photoresist coating. The photomask has areas opaque and transparent to activating radiation that define an image desired to be transferred to the underlying substrate. A relief image is provided by development of the latent image pattern in the resist coating. The use of photoresists is generally well-known to those skilled in the art.

Known photoresists can provide features having resolution and size sufficient for many existing commercial applications. However for many other applications, the need exists for new photoresists that can provide highly resolved images of sub-micron dimension.

Various attempts have been made to alter the make-up of photoresist compositions to improve performance of functional properties. Among other things, a variety of photoactive compounds have been reported for use in photoresist compositions. See, for example, U.S. Pat. No. 7,304,175 and U.S. Pat. App. Pub. No. 2007/0027336. In particular, tailored photoacid generators (PAGs) having controlled acid diffusion and improved miscibility with polymers are very important to meet the challenges for resist materials raised by high resolution lithography. For example, certain defects such as T-topping, foot formation and notching may arise in imaged photoresist films if the PAG is not uniformly distributed within the resist film. It is believed that the structure of the PAG anion plays a critical role in the overall performance of a photoresist by affecting the interaction of the photoacid generator with other photoresist components. These interactions, in turn, have remarkable effects on diffusion characteristics of the photogenerated acid. PAG structure and size greatly affect the homogenous distribution of the PAG in the photoresist film.

There remains a need for PAG anions which posses certain structural, chemical and physical characteristics to improve photoacid diffusion rate and provide better miscibility with other photoresist components.

The present invention provides new photoacid generator compounds that comprise one or more oxa adamantan-one lactone groups. Preferred oxa adamantan-one lactone groups include those of the following general formula (1):

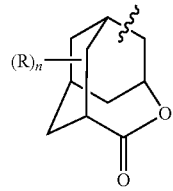

(1)

wherein each R is the same or different and is a hydrogen or non-hydrogen substituent, and n is an integer from zero to 6.

Also provided by the present invention are photoacid generator compounds that comprise one or more of the above oxa adamantan-one lactone groups. In the case of an ionic photoacid generator (e.g. a sulfonium, iodonium or other onium salt), one or more oxa adamantan-one lactone groups may be present on one or more of the anion and cation components of the PAG.

The present invention further provides resins that comprises one or more of the above oxa adamantan-one lactone groups.

Still further, the present invention provides photoresist composition that comprise (a) one or more photoacid generator compounds, wherein at least one photoacid generator comprises an oxa adamantan-one lactone group(s), (b) one or more resins that comprise one or more of the above oxa adamantan-one lactone group(s), and/or (c) a mixture of (a) and (b).

As used herein, the term "alkyl" includes linear, branched and cyclic alkyl. The term "(meth)acrylate" includes both acrylate and methacrylate. Likewise, the term "(meth) acrylic" includes acrylic and methacrylic. The articles "a" and "an" refer to the singular and the plural. The following abbreviations shall have the following meanings: ° C.=degrees Celsius; nm=nanometers; μm=micron=micrometer; cm=centimeter; mJ=milliJoules; wt %=weight percent; and PAG=photoacid generator. All ratios are molar ration unless otherwise indicated.

Photoacid generator compounds of the invention include both ionic and non-ionic compounds. Generally preferred PAG compounds of the invention that can may generate a fluorosulfonic acid, particularly an α,α-difluoroalkyl sulfonic acid, upon photoactivation of: onium compounds such as sulfonium and iodonium compounds; sulfonate compounds such as N-oxyimidosulfonates, N-oxyiminosulfonates, phenolic sulfonates arylalkylsulfonates particularly benzylic sulfonates; disulfones such as diazosulfones and α,α-methylenedisulfones; and disulfonylhydrazines. Ionic photoacid generator compounds, particularly PAG compounds that generate a sulfonic acid (—SO$_3^-$) upon photoactivation are preferred.

The photoacid generator compounds (or photoacid generators) of the present invention comprise one or more oxa adamantan-one lactone groups. Preferred oxa adamantan-one lactone groups include those of the following general formula (1):

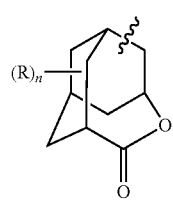

(1)

wherein each R is the same or different and is a hydrogen or non-hydrogen substituent, and n is an integer from zero to 6. Preferably, each R is chosen from hydrogen, hydroxy, cyano, $(C_1\text{-}C_{12})$alkoxy, $(C_1\text{-}C_{12})$carbonyloxy, $(C_1\text{-}C_{12})$alkyl or fluoro$(C_1\text{-}C_{12})$alkyl. More specifically, the present photoacid generators comprising an oxa adamantan-one lactone group have the 4-oxa-5-homoadamantan-5-one lactone formula (2)

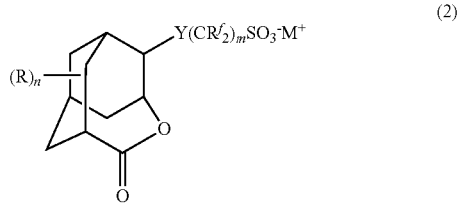

(2)

wherein each R is the same or different and is a hydrogen or non-hydrogen substituent; Y is a connecting group; each $R^f$ is independently chosen from hydrogen, fluorine, and fluoro $(C_1\text{-}C_{10})$alkyl; M is a cation; n is an integer from zero to 6; and m is an integer of 1 to 10. As used herein, fluoroalkyl includes alkyl groups having from one to all of its hydrogen atoms replaced with fluorine. Each R is preferably chosen from hydrogen, hydroxy, cyano, $(C_1\text{-}C_{-20})$alkoxy, $(C_1\text{-}C_{-20})$carbonyloxy, $(C_1\text{-}C_{-20})$alkyl and fluoro$(C_1\text{-}C_{-20})$alkyl. More preferably, each R is chosen from hydrogen, hydroxy, cyano, $(C_1\text{-}C_{12})$alkoxy, $(C_1\text{-}C_{-10})$carbonyloxy, $(C_1\text{-}C_{-10})$alkyl and $(C_1\text{-}C_{-12})$fluoroalkyl. Y may be any suitable connecting group, and is preferably chosen from a chemical bond, —O—, and $Y^1$. $Y^1$ is a group having from 1 to 30 carbon atoms, which may optionally contain one or more heteroatoms chosen from O, S, and N. More preferably, $Y^1$ is chosen from a group having from 1 to 20 carbon atoms, which may optionally contain one or more heteroatoms chosen from O, S, and N. Oxygen is the preferred heteroatom for $Y^1$. Each $R^f$ is independently chosen from hydrogen, fluorine, and fluoro$(C_1\text{-}C_{10})$alkyl, more preferably each $R^f$ is chosen from hydrogen, fluorine and fluoro $(C_1\text{-}C_6)$alkyl, and even more preferably hydrogen and fluorine. Preferably, at least one $R^f$ is chosen from fluorine or fluoro$(C_1\text{-}C_{10})$alkyl. Preferably, M is an onium cation, more preferably M is chosen from a sulfonium cation and an iodonium cation, and most preferably, M is a sulfonium cation.

In the compounds of formula (2), each R is preferably chosen from hydrogen, hydroxy, cyano, $(C_1\text{-}C_{-20})$alkoxy, $(C_1\text{-}C_{-20})$carbonyloxy, $(C_1\text{-}C_{-20})$alkyl and $(C_1\text{-}C_{-20})$fluoroalkyl. More preferably, each R is chosen from hydrogen, hydroxy, cyano, $(C_1\text{-}C_{-12})$alkoxy, $(C_1\text{-}C_{-10})$carbonyloxy, $(C_1\text{-}C_{-10})$alkyl and $(C_1\text{-}C_{-12})$fluoroalkyl. Exemplary alkoxy groups include methoxy, ethoxy, propoxy, butoxy, pentoxy, methoxyethyl, methoxypropyl, ethoxyethyl, ethoxypropyl, tert-butoxy, neopentoxy, and the like. Exemplary carbonyloxy groups include carboxyl, acetoxy, and —C(O)O—$(C_1\text{-}C_{29})$alkyl. Exemplary alkyl groups include methyl, ethyl, n-propyl, iso-propyl, n-butyl, sec-butyl, iso-butyl, tert-butyl, n-pentyl, neo-pentyl, cyclopentyl, methylcyclopentyl, n-hexyl, cyclohexyl, methylcyclohexyl, heptyl, cycloheptyl, octyl, cyclooctyl, and the like. Exemplary fluoroalkylgroups include fluoromethyl, difluoromethyl, trifluoromethyl, fluoroethyl, difluoroethyl, perfluoroethyl, difluoropropy, trifluoropropyl, perfluoropropyl, difluorobutyl, tetrafluorobutyl, perfluorobutyl, and the like.

Connecting group Y in formula (2) is preferably chosen from a chemical bond, —O—, and $Y^1$. $Y^1$ is a group having from 1 to 30 carbon atoms, which may optionally contain one or more heteroatoms chosen from O, S, and N. More preferably, $Y^1$ is a chosen from a group having from 1 to 20 carbon atoms, which may optionally contain one or more heteroatoms chosen from O, S, and N. Oxygen is the preferred heteroatom for $Y^1$. Exemplary connecting groups of $Y^1$ include —C(O)O—, —C(O)—CH$_2$O—, —O—C(O)—, —O—CH$_2$C(O)—, —OCH$_2$—C(O)O—, —NH—C(O)—, —S(O)$_2$O—, —O—S(O)$_2$—, —NH—S(O)$_2$, —(SO)$_2$—NH—, —C(O)O—CH$_2$CH$_2$—, —C(O)—CH$_2$—, —O—C(O)—CH$_2$CH$_2$—, and the like.

Any suitable fluoro$(C_1\text{-}C_{10})$alkyl may be used as the $R^f$ group. Any fluoroalkyl groups having 1-10 carbons described above for R may suitably be used as the $R^f$ group.

Suitable cations for M are sulfonium cations of formula (3) and iodonium cations of formula (4):

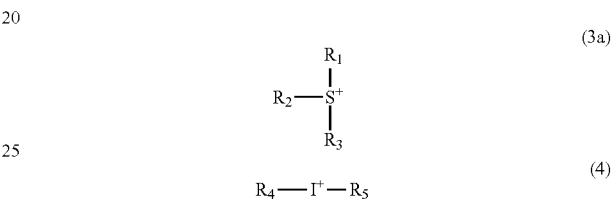

wherein $R_1$ to $R_3$ each independently represents a carbocylic aryl group which may contain a substituent group (that is, may be optionally substituted), an allyl group, a$(C_1\text{-}C_{20})$ alkyl group which may contain a substituent group (that is may be optionally substituted) such as a perfluoro$(C_1\text{-}C_{20})$ alkyl group or a $(C_6\text{-}C_{15})$aralkyl group such as benzyl and phenethyl, preferably at least one of $R_1$ to $R_3$ represents a carbocyclic aryl group; alternatively, $R_1$ and $R_2$ are mutually bonded to form a ring together with the sulfur ion to which they are attached, $R_3$ represents a carbocyclic aryl group which may contain a substituent group (that is, may be optionally substituted), a $C_1\text{-}C_{20}$)alkyl group which may contain a substituent group (that is, may be optionally substituted); and $R_4$ and $R_5$ each independently represents a carbocyclic aryl group which may contain a substituent group (that is, may be optionally substituted).

Preferred sulfonium cations are those of formulae (3a) to (3f):

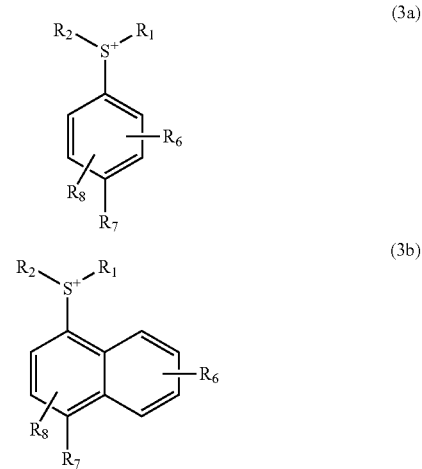

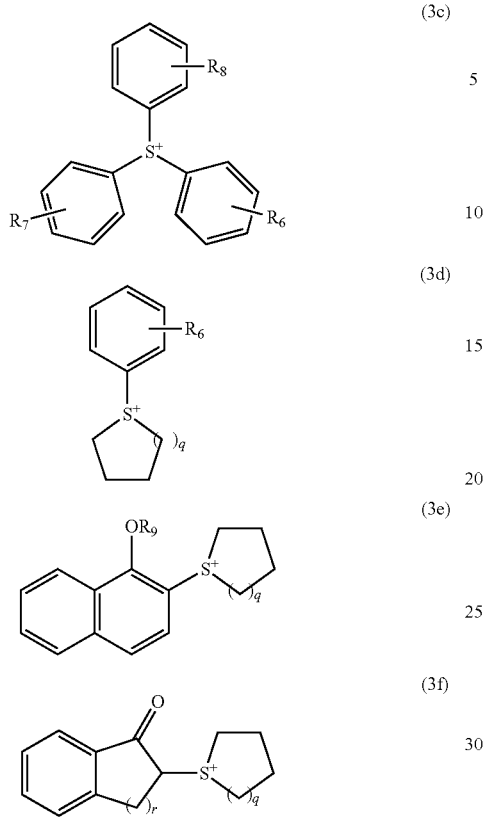

wherein $R_1$ and $R_2$ are as described above for formula (3); $R_6$ to $R_8$ are independently chosen from hydrogen, hydroxy, $(C_1\text{-}C_{20})$alkyl group, halogen, $(C_1\text{-}C_{20})$alkoxy group, aryl, thiophenoxy, thio$(C_1\text{-}C_{20})$alkoxy group and $(C_1\text{-}C_{20})$ alkoxycarbonyl; $R_9$ is a $(C_1\text{-}C_{20})$alkyl; q=1-10; and r=1-2. Each of $R_6$ to $R_8$ may independently contain an acid labile group, a base labile group or a base soluble group.

Particularly preferred sulfonium cations of formula (3c) are shown by structures $C_1\text{-}C_6$, particularly suitable sulfonium cations of formula (3d) are shown by structures D1 and D2, and a particularly suitable structure of formula (3e) is shown by structure E1.

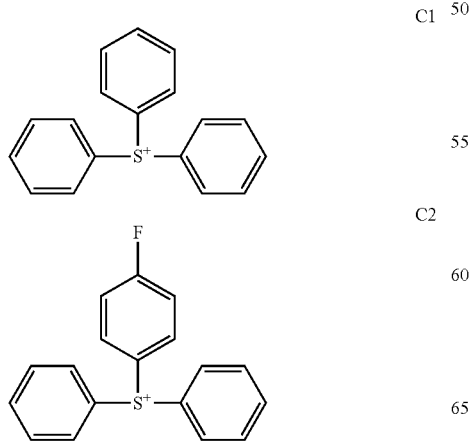

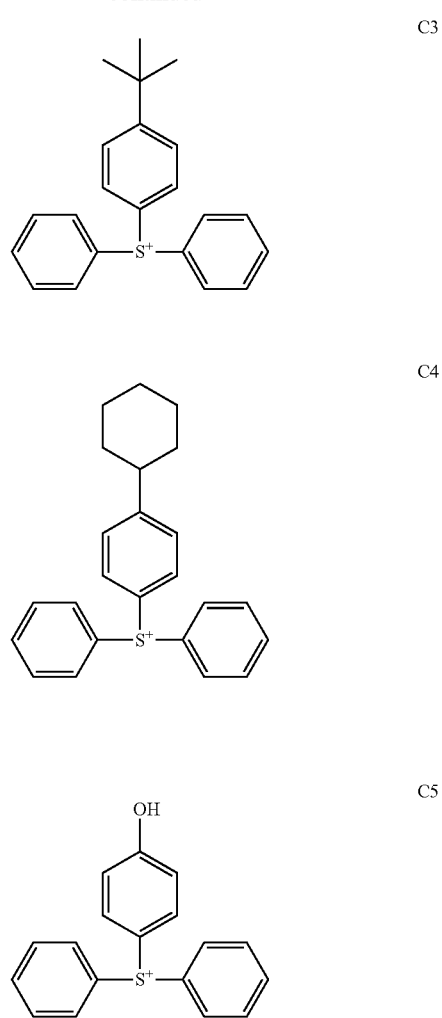

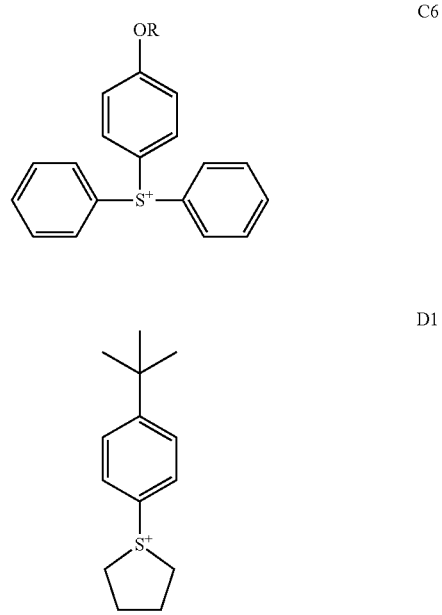

-continued

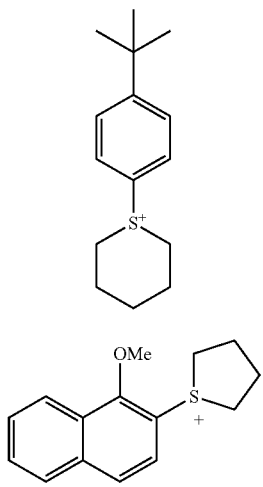

D2

E1

It is further preferred that the oxa adamantan-one lactone group comprises at least one of a fluoromethylene group (—CHF—), difluoromethylene group (—CF$_2$—), or a fluoroalkyl substituted carbon adjacent to a sulfonate (—SO$_3^-$—) group (that is, in the alpha or c' position). More preferably, the present oxa adamantan-one lactone group comprises a difluoromethylene group (—CF$_2$—) adjacent to a sulfonate (—SO$_3^-$—) group. Particularly preferred compounds of formula (2) have the general formula (2a):

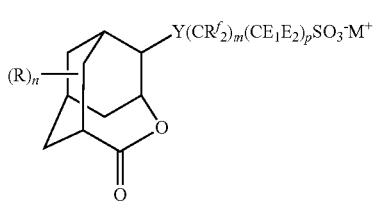

(2a)

wherein R, Y, R$^f$, M, m and n are as described above for formula (II); wherein E$_1$ is hydrogen, fluorine, or fluoro(C$_1$-C$_{10}$)alkyl; E$_2$ is a fluorine, or fluoro(C$_1$-C$_{10}$)alkyl; and p is an integer from 1 to 6. Preferably, E$_1$ is fluorine or fluoro (C$_1$-C$_{10}$)alkyl, and more preferably fluorine. It is preferred that p is an integer from 1 to 4, more preferably from 1 to 3, and even more preferably from 1 to 2. It is further preferred that m=0-4, and more preferably 0-2. Particularly preferred compounds of formula 2a are those wherein E$_1$=fluorine; R$^f$=hydrogen; Y is chosen from a chemical bond, —OC(O)—, —OC(O)CH$_2$O—, and —OCH$_2$C(O)O—; p=1-2; and m=0-2.

Particularly preferred PAGs of the present invention are those having the formula

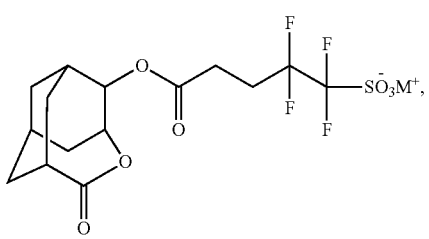

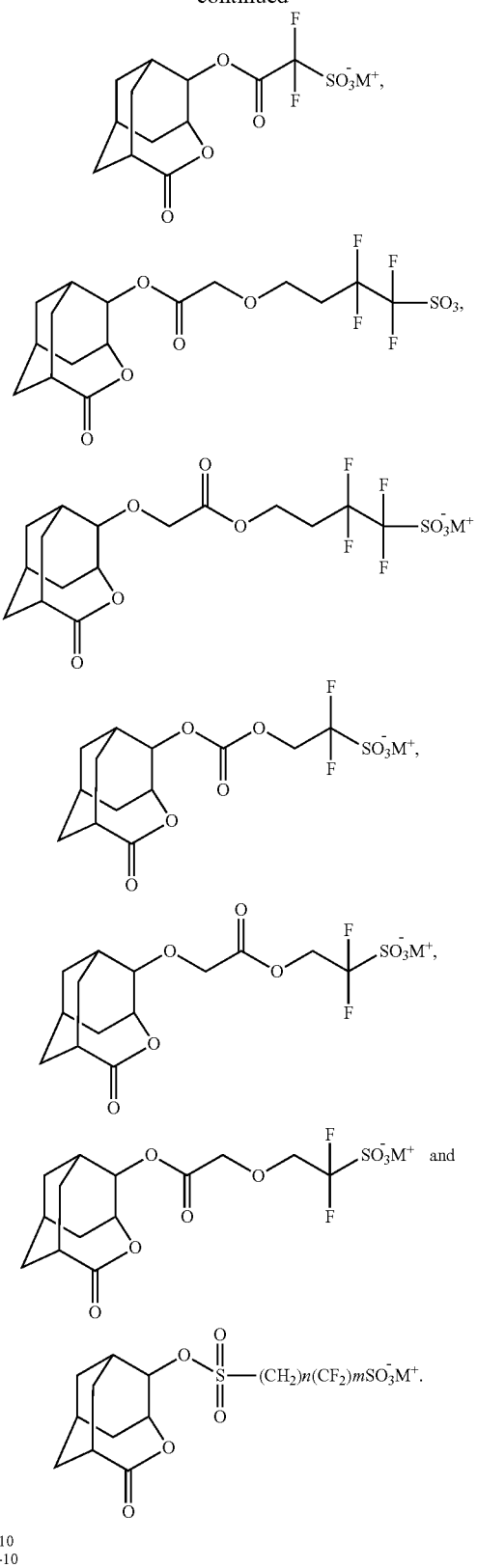

n = 0-10
m = 1-10

The PAGs of the present invention are preferably prepared according to Scheme 1, which uses compound A1 as a starting material.

Scheme 1

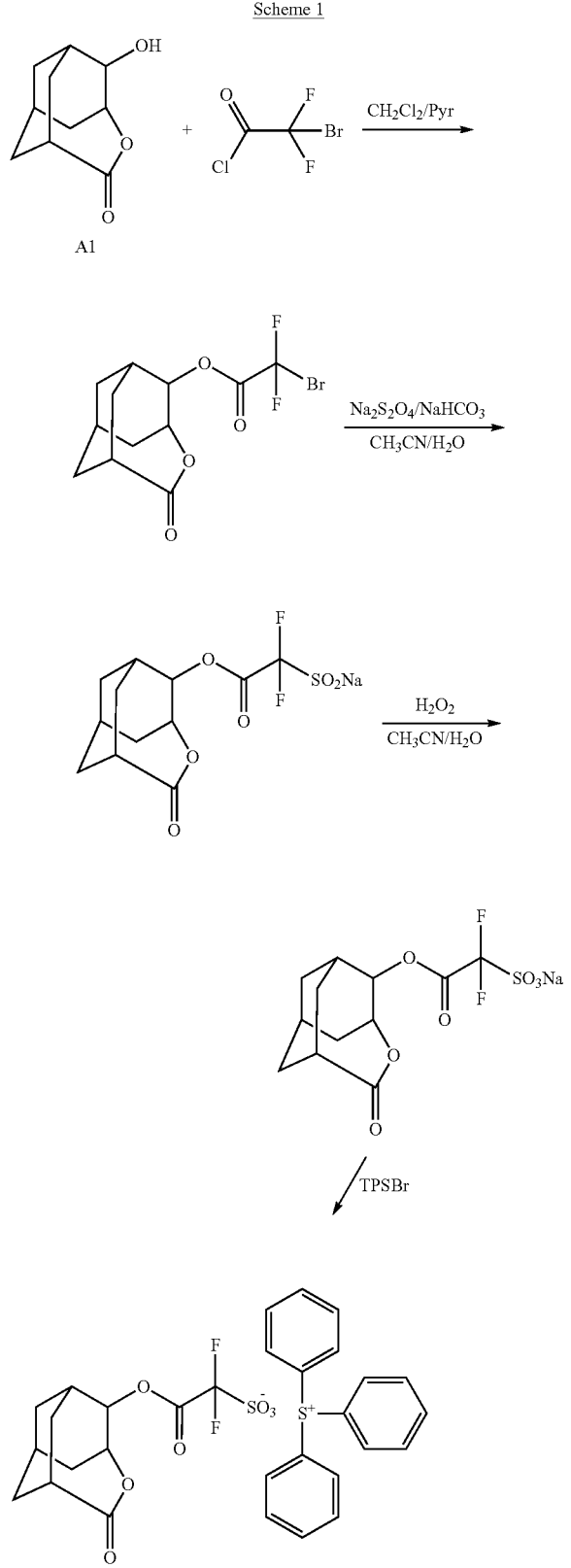

In a similar manner, compounds of the structures A2 or A3 may also be used to prepare compounds of the present invention.

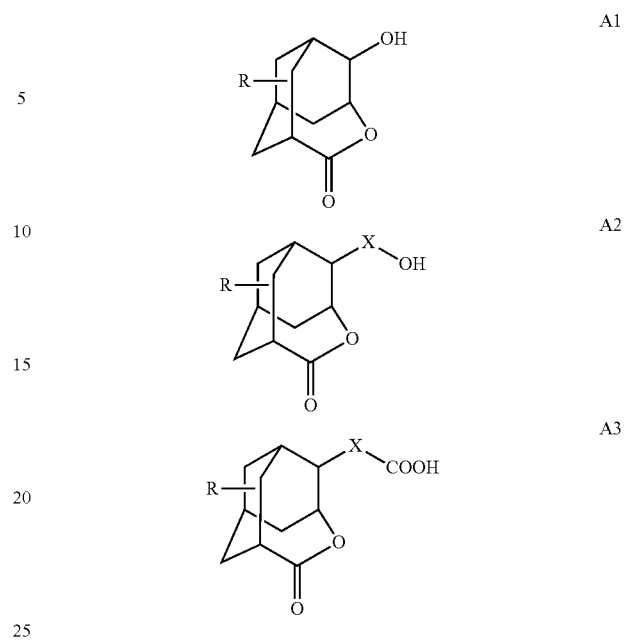

In those structures A1, A2 and A3, R is as described above, and may be present multiple occurrences as permitted by valances; X is bridging group which may be a chemical bond, $(C_1$-$C_{12})_2$alkyl, fluoro$(C_1$-$C_{12})$alkyl chain, $(C_1$-$C_{12})$alkoxy or $(C_1$-$C_{12})$carbonyloxyalkyl. Preferably, each R is chosen from hydrogen, hydroxy, cyano, $(C_1$-$C_{12})$alkoxy, $(C_1$-$C_{12})$carbonyloxy, $(C_1$-$C_{12})$alkyl and fluoro$(C_1$-$C_{12})$alkyl. Especially preferred compounds of formula (2) and (2a) may be synthesized via the above compounds A1, A2 and/or A3. Connecting group X in structures A1, A2 and A3 is preferably chosen from a chemical bond, —O—, and $X^1$. $X^1$ is a group having from 1 to 30 carbon atoms, which may optionally contain one or more heteroatoms chosen from O, S, and N. More preferably, $X^1$ is a chosen from a group having from 1 to 20 carbon atoms, which may optionally contain one or more heteroatoms chosen from O, S, and N. Oxygen is the preferred heteroatom for $X^1$. Exemplary connecting groups of $X^1$ include —C(O)O—, —C(O)—CH₂O—, —O—C(O)—, —O—CH₂C(O)—, —OCH₂—C(O)O—.

Preferably, the present invention also provides polymerizable monomers and resins that comprise one or more oxa adamanatan-one lactone groups. Particularly preferred monomers are depicted by the following formulae (5a) to (5c). Particularly preferred resins are shown by the resins below having repeat units that comprise structures (6a) to (6c).

(5a)

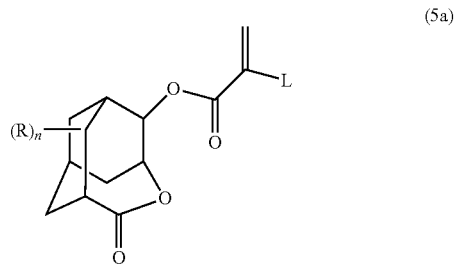

-continued (5b)
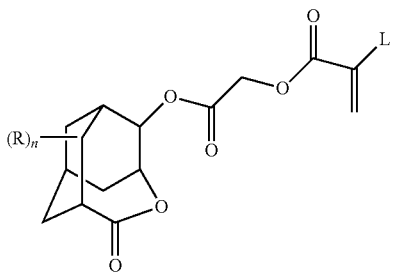

(5c)
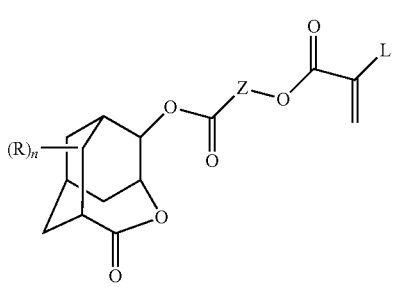

(6a)
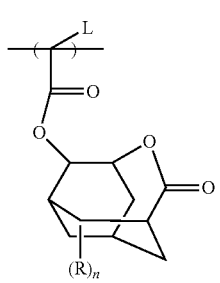

(6b)
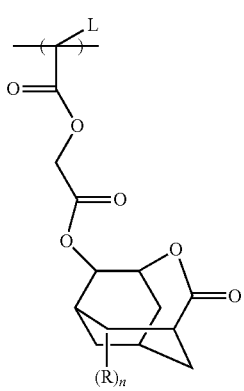

(6c)
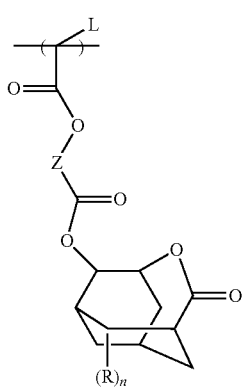

In the above structures (5a)-(5c) and (6a)-(6c), L can be any suitable group, and is preferably hydrogen, methyl, fluorine or trifluoromethyl. R can be present one or multiple times as permitted by available valances and each R may be the same or different hydrogen or non-hydrogen substituent such as hydroxy, cyano, ($C_1$-$C_{12}$)alkoxy, ($C_1$-$C_{12}$)carbonyloxy, ($C_1$-$C_{12}$)alkyl or fluoro($C_1$-$C_{12}$)alkyl Z1 is a bridging group that may contain at least one methylene unit.

Such resins may be formed by any number of methods, for example, by polymerizing a monomer that comprises one or more such oxa adamantan-one lactone groups to thereby provide a resin repeat unit that comprise one or more oxa adamantan-one lactone groups. Such monomers can be polymerized with one or more other distinct monomers to thereby provide a copolymer (2 distinct repeat units), terpolymer (3 distinct repeat units), tetrapolymer (4 distinct repeat units), pentapolymer (5 distinct repeat units), and the like.

Alternatively, rather than polymerizing a monomer that comprises one or more such oxa adamantan-one lactone groups, a pre-formed resin may be reacted to graft onto the resin one or more oxa adamantan-one lactone groups.

For use in a positive-acting photoresist composition, preferably resins of the invention comprise photoacid-labile groups. An oxa adamanatan-one lactone moiety suitably may be a component of such photoacid-labile groups, e.g. a photoacid-labile photo-cleavage product may comprise an oxa adamanatan-one lactone moiety.

It is believed that at least certain of the present resins that comprise one or more oxa adamantan-one lactone groups can provide high levels of resistance to plasma etchants. It is also believed that at least certain of the present resins that comprise one or more oxa adamantan-one lactone groups can provide high glass transition temperature which is advantageous for high resolution and lower line width roughness (LWR).

In certain preferred aspects of the invention, ester groups comprising an oxa adamantan-one lactone moiety will link to a secondary carbon of the adamantan-one lactone moiety, as exemplified by the above structures (5a), (5b), (5c), (6a), (6b), and (6c).

Syntheses of precursors for oxa adamantan-one lactone compounds and monomers may be suitably conducted by procedures that include those disclosed in *J. Am. Chem. Soc.*, Vol. 108, No. 15. 1986, 4484 and *J. Org. Chem.*, 1981, 46, 5332-5336.

Preferably, PAGs of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions.

Preferred imaging wavelengths are sub-300 nm, and more preferably sub-200 nm such as 193 nm and EUV. Other sub-200 nm wavelengths may suitably be used.

Photoresists of the invention contain an imaging-effective amount of one or more of the present PAGs. Alternatively, photoresists of the invention may contain one or more resins comprising as polymerized units an oxa adamantan-one lactone group. In yet a further alternative, photoresists of the invention may comprise both an imaging-effective amount of one or more of the present PAGs and one or more resins comprising as polymerized units an oxa adamantan-one lactone group.

Photoresists of the invention typically comprise a resin binder (polymer), a PAG as described above, and optionally one or more other components such as a base (quencher), solvent, actinic and contrast dyes, anti-striation agents, plasticizers, speed enhancers, sensitizers, and the like. More than one of any of these photoresist components may be used. Such optional additives if used are typically present in the composition in minor amounts such as from 0.1 to 10 wt % based on total solids of the photoresist composition. Preferably the resin binder has functional groups that impart alkaline aqueous developability to the photoresist composition. For example, preferred are resin binders that comprise polar functional groups such as hydroxyl or carboxylate. Preferably the resin binder is used in a resist composition in an amount sufficient to render the resist developable with an aqueous alkaline solution.

Preferred resins that have acid-labile deblocking groups for use in a positive-acting chemically-amplified photoresist of the invention have been disclosed in European Patent Application 0829766 (resins with acetal and ketal resins) and European Patent Application EP0783136 (terpolymers and other copolymers including units of 1) styrene; 2) hydroxystyrene; and 3) acid labile groups, particularly alkyl acrylate acid labile groups such as t-butylacrylate or t-butylmethacrylate). In general, resins having a variety of acid labile groups will be suitable, such as acid sensitive esters, carbonates, ethers, imides, etc. The photoacid labile groups will more typically be pendant from a polymer backbone, although resins that have acid labile groups that are integral to the polymer backbone also may be employed.

Preferred imaging wavelengths of the photoresists of the invention include sub-300 nm wavelengths, such as 248 nm, and more preferably sub-200 nm wavelengths, such as 193 nm and EUV, although other sub-200 nm wavelengths may be used.

For imaging at wavelengths greater than 200 nm, such as 248 nm, phenolic resins are typically preferred. Preferred phenolic resins are poly(vinylphenols) which may be formed by block polymerization, emulsion polymerization or solution polymerization of the corresponding monomers in the presence of a catalyst. Particularly preferred resins useful for imaging at these wavelengths include: i) polymers that contain polymerized units of a vinyl phenol and an alkyl (meth)acrylate, where the polymerized alkyl(meth)acrylate units can undergo a deblocking reaction in the presence of photoacid. Exemplary alkyl(meth)acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl (meth)acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups.

A preferred optional additive of photoresists of the invention is an added base, particularly tetrabutylammonium hydroxide (TBAH) or various amides, which can enhance resolution of a developed resist relief image. The added base is suitably used in relatively small amounts, e.g. 1 to 10 wt % relative to the PAG, more typically 1 to 5 wt %. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The present photoresist compositions typically comprise a solvent. Suitable solvents include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as acetone, methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

The photoresists of the invention are generally prepared following known procedures. For example, a resist of the invention can be prepared as a coating composition by dissolving the components of the photoresist in a suitable solvent. The resin binder component of resists of the invention are typically used in an amount sufficient to render an exposed coating layer of the resist developable such as with an aqueous alkaline solution. More particularly, a resin binder will suitably comprise 50 to 90 wt % of total solids of the resist. The photoactive component should be present in an amount sufficient to enable generation of a latent image in a coating layer of the resist. More specifically, the photoactive component will suitably be present in an amount of from 1 to 40 wt % of total solids of a resist. Typically, lesser amounts of the photoactive component will be suitable for chemically amplified resists.

The desired total solids content of the present photoresist compositions will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

Preferred negative-acting photoresist compositions of the invention comprise a mixture of materials that will cure, crosslink or harden upon exposure to acid, and a photoactive component of the invention. Preferred negative acting compositions comprise a resin binder such as a phenolic or non-aromatic resin, a crosslinker component and a photoactive component of the invention. Such compositions and the use thereof has been disclosed in European Patent Applications EP 0164248 and EP 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by Cytec under the trade names Cymel 300, 301 and 303. Glycoluril resins are sold by Cytec under the trade names Cymel 1170, 1171, 1172, urea-based resins are sold under the trade names of Beetle 60, 65 and 80, and benzoguanamine resins are sold under the trade names Cymel 1123 and 1125.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Printed circuit board substrates such as copper clad laminates are also suitable substrates. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating.

The photoresist layer (with overcoated barrier composition layer, if present) may be preferably exposed to activating radiation in an immersion lithography system, i.e. where the space between the exposure tool (particularly the projection lens) and the photoresist coated substrate is occupied by an immersion fluid, such as water or water mixed with one or more additives such as cesium sulfate, which can provide a fluid of enhanced refractive index. Preferably the immersion fluid (e.g., water) has been treated to avoid bubbles, e.g. water can be degassed to avoid nanobubbles. References herein to "immersion exposing" or other similar term indicates that exposure is conducted with such a fluid layer (e.g., water or water with additives) interposed between an exposure tool and the coated photoresist composition layer.

The exposure energy should be sufficient to effectively activate the photoactive component of the radiation sensitive system to produce a patterned image in the resist coating layer. Suitable exposure energies typically range from about 1 to 300 mJ/cm$^2$. Suitable exposure wavelengths include sub-300 nm such as 248 nm or sub-200 nm such as 193 nm or EUV, or other higher energy exposure sources also may be employed such as electron beam, ion beam and x-ray radiation, and other ionizing radiation. Suitable post-exposure bake temperatures are from 50° C. or greater, more specifically from 50 to 140° C. For an acid-hardening negative-acting resist, a post-development bake may be employed if desired at temperatures of from 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The invention also provide methods for forming relief images of the photoresists of the invention, including methods for forming highly resolved patterned photoresist images (for example, a patterned line having essentially vertical sidewalls) of sub-quarter μm dimensions or less, such as sub-0.2 or sub-0.1 μm dimensions.

The invention further provides articles of manufacture comprising substrates such as a microelectronic wafer or a flat panel display substrate having coated thereon the photoresists and relief images of the invention.

EXAMPLE 1

Photoresist Preparation and Lithographic Processing

A photoresist of the invention is prepared by mixing the following components with amounts expressed as weight percent based on total weight of the resist compositions:

| Resist components | Amount (wt. %) |
| --- | --- |
| Resin binder | 15 |
| Photoacid generator | 3 |
| Ethyl lactate | 81 |

The resin binder is a terpolymer of 2-methyl-2-adamantyl methacrylate/beta-hydroxy-gamma-butyrolactone methacrylate/cyano-norbornyl methacrylate. The photoacid generator is the compound shown in Scheme 1 above. The resin and PAG components are admixed in ethyl lactate solvent.

The formulated resist composition is spin coated onto an antireflective coating layer disposed on a 150 mm (six inch) silicon wafers and softbaked via a vacuum hotplate at 130° C. for 60 seconds. The resist coating layer is exposed through a photomask at 193 nm, and then the exposed coating layers are post-exposure baked at 130° C. for 90 seconds. The coated wafers are then treated with 0.26N aqueous tetramethylammonium hydroxide solution to develop the imaged resist layer.

EXAMPLE 2

Synthesis of Photoacid Generator PAG-Al

Photoacid generator PAG-Al was prepared by a five-step synthesis as outlined in Scheme 2 and the following paragraphs. The detailed synthetic process is presented below. Starting material 2-anti-hydroxy-4-oxa-5-homoadamatan-5-one (1) was prepared following the procedure published by Helmut Duddeck and coworkers in *J. Org. Chem.* 1981, 46, 5332-5336.

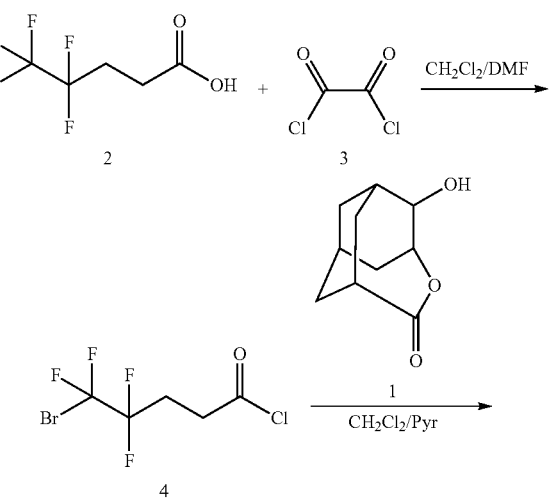

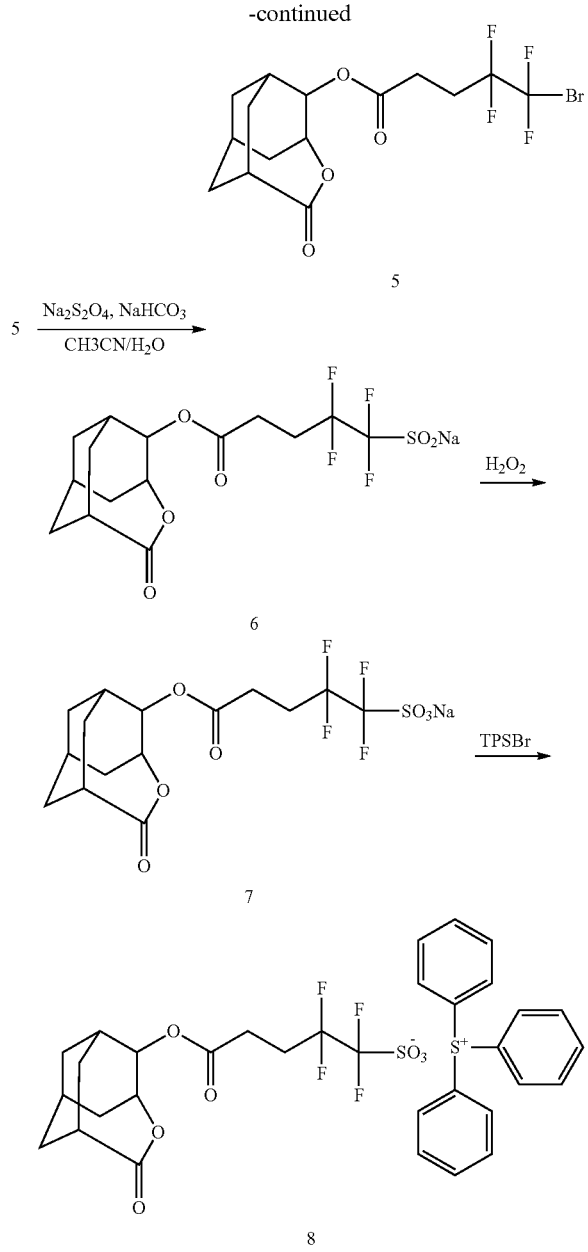

Compound 6 was prepared using the following procedure. To a round bottom flask equipped with a thermometer, overhead stirrer and condenser with $N_2$ gas inlet, 14 g (33.55 mmol) of compound 5 was dissolved in 75 mL of acetonitrile and poured into an solution of sodium dithionite (12.85 g) and sodium hydrogen carbonate (8.40 g) in 100 mL of water. The reaction mixture was heated to 70° C. for about 18 hours and then cooled to room temperature. The aqueous layer was then removed and the acetonitrile solution (upper layer) that contained product 6 was used in the next step assuming 100% conversion. To the acetonitrile solution of the sulfinate derivative 6 was added 50 mL of water followed by 1.5 equivalent of an aqueous solution of hydrogen peroxide and the reaction was stirred at room temperature for 48 hours. Then sodium chloride (50 g) and sodium sulfite (10 g) were added. The mixture was allowed to separate into two layers. The upper acetonitrile layer was separated, dried over $MgSO_4$, filtered and the solvent was removed under reduced pressure to produce the product 7 as white waxy solid. The overall isolated yield for the conversion of 5 to 7 was 44%.

The synthesis of the photoacid generator PAG-A1 (8) was achieved as follows: To a biphase system composed of 50 mL methylene chloride and 50 mL water was added 5 g (11.33 mmol) 7 and 3.9 g (11.36 mmol) of triphenyl sulfonium bromide (TPSBr) and the reaction mixture was stirred at room temperature for 18 hours. The organic phase was separated and washed with deionized water (5×50 mL). The separated organic phase was concentrated and poured into methyl t-butyl ether to produce the target photoacid generator PAG-A1 (8). A second precipitation in methyl t-butyl ether produce pure product in 50% isolated yield. Samples of the PAG were assayed for purity using the HPLC MS. The cation purity as detected by UV at 230 nm is 99.8% and the purity detected by positive ion mass spectrometry is 99.4%. The anion purity as measured by negative ion liquid chromatography mass spectrometry (LCMS) was 100%.

EXAMPLE 3

Photoacid generator PAG-A2 was prepared by a five-step synthesis as outlined in Scheme 3 and the following paragraphs. The detailed synthetic process is presented below.

To a solution of 5-bromo-4,4,5,5-tetrafluoropentanoic acid (2, 10 g, 39.52 mmol) in 100 mL of methylene chloride was added few drops of N,N-dimethyl formamid followed by oxalyl chloride (3, 5 g, 39.50 mmol) and the reaction mixture was stirred at room temperature for 2 hours. The product 5-bromo-4,4,5,5-tetrafluoropentanoyl chloride (4) was not isolated. To the above reaction mixture was added 2-anti-hydroxy-4-oxa-5-homoadamatan-5-one (1, 7.2 g, 39.51 mmol) followed by one equivalent of pyridine. The reaction mixture was stirred at room temperature for 16 hours. The content of the reaction mixture was transferred to a separation funnel and the methylene chloride solution was washed with 100 mL of 1N aqueous HCl, and then washed with water (2×100 mL). The organic phase was separated, dried over $MgSO_4$, filtered and the solvent was removed under reduce pressure to produce the 14 g of the crude product 5 which was used in the next step without further purification.

Scheme 3

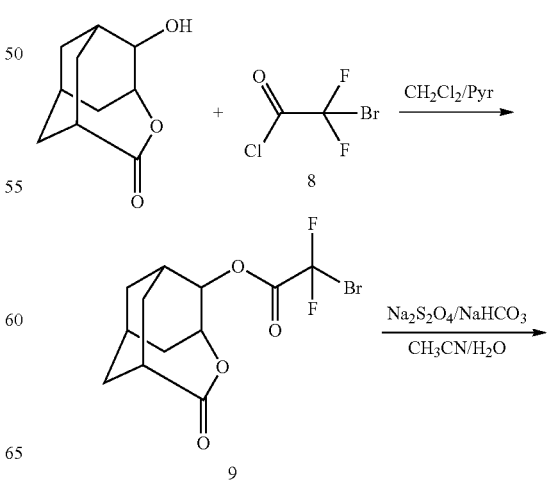

-continued

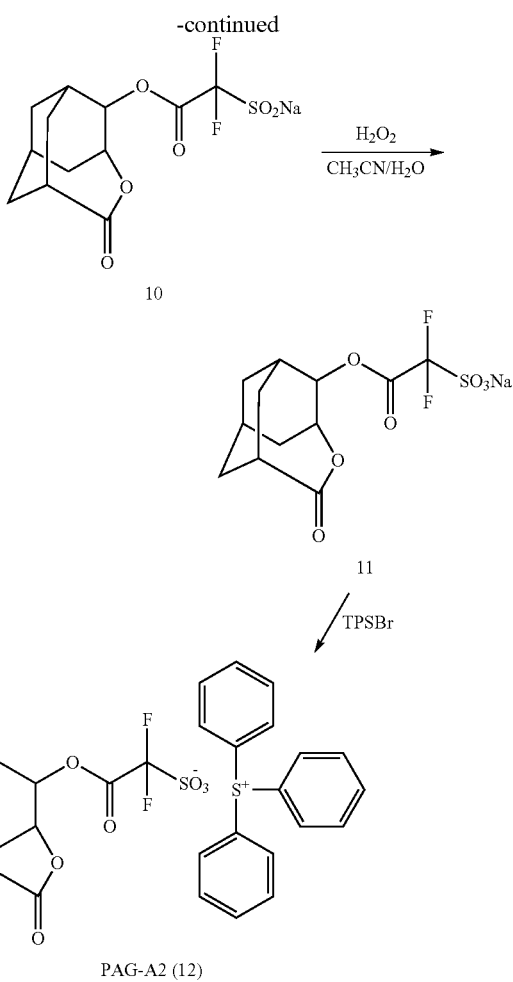

To a mixture 2-anti-Hydroxy-4-oxa-5-homoadamatan-5-one (1, 20 g, 0.1 mol) and 2-bromo-2,2-difluoroacetyl chloride (8, 23.34 g, 0.12 mol) in 150 mL of acetonitrile was added pyridine (9.55 g, 0.12 mol) and the reaction mixture was stirred at room temperature for 16 hours. The solvent was completely removed and the remaining residue was dissolved in 150 mL methylene chloride. The methylene chloride solution was transferred to a separation funnel and washed with 100 mL of 1N aqueous HCl, and then washed with water (2×100 mL). The organic phase was separated, dried over MgSO$_4$, filtered and the solvent was removed under reduce pressure to produce the 36.7 g of the crude product 9 which was used in the next step without further purifications. In the next step compound 10 was prepared using the following procedure. To a round bottom flask equipped with a thermometer, overhead stirrer and condenser w/N$_2$ gas inlet, 36.7 g (0.1 mol) of 9 was dissolved in 150 mL of acetonitrile and poured into a solution of sodium dithionite (37.6 g, 0.215 mol) and sodium hydrogen carbonate (18.0 g, 0.215 mol) in 150 mL of water. The reaction mixture was stirred at room temperature for 16 hours. $^1$H-NMR of a sample from the reaction mixture indicated the presence of the expected product 10. Sodium chloride (100 g) was added to the reaction mixture and the aqueous layer was then removed and the acetonitrile solution (upper layer) that contained product 10 was used in the next step assuming 100% conversion. To the acetonitrile solution of the sulfinate derivative 10 was added 50 mL of water followed by 22 g of 30% aqueous solution of hydrogen peroxide and the reaction was stirred at room temperature for 48 hours. Then sodium chloride (50 g) and sodium sulfite (10 g) were added. The mixture was allowed to separate into two layers. The upper acetonitrile layer was separated, dried over MgSO$_4$, filtered and the solvent was removed under reduced pressure to produce the product 11 as white waxy solid.

The synthesis of the photoacid generator PAG-A2 (12) was achieved as follows: To a biphase system composed of 75 mL methylene chloride and 75 mL water was added 25 g (69.0 mmol) of 11 and 23.6 g (68.7 mmol) of triphenyl sulfonium bromide (TPSBr) and the reaction mixture was stirred at room temperature for 18 hours. The organic phase was separated and washed with deionized water (5×50 mL). The separated organic phase was concentrated and poured into methyl t-butyl ether to produce the target photoacid generator PAG-A2 (12). A second precipitation from acetone solution with methyl t-butyl ether produced 28 g of pure product (67.5%) yield. $^1$H NMR (acetone-d6) δ: 7.90 (m, 15H), 5.06 (1H, m), 4.32 (1H, m), 2.89 (m, 1H), 2.4-1.5 (10H, complex); $^{19}$F NMR (acetone-d6): $^{19}$F NMR (acetone-d6) δ: −111.1 (CF$_2$SO$_3$).

EXAMPLE 4

Acid Diffusion Measurement

Acid diffusion measurements were taken using a bilayer system. In this process flow, an organic antireflective coating layer was disposed on a silicon substrate. An acid detection layer, composed of a conventional 193 nm photoresist, was disposed on the antireflective coating layer. An acid source layer, which is composed of an acid inert polymer and the photoacid generator in study, was then disposed on the acid detection layer. Upon exposure using a 193 nm wavelength source, a photoacid is generated in the acid source layer. Subsequent heating (post bake exposure or PEB) leads to acid diffusion from the acid source layer to the acid detection layer0, where deprotection and solubility switching events occur. Subsequent development with aqueous base leads to film loss on the exposed area. The diffusivity of the PAG, D, is defined by Fick's law of diffusion: $D=(\Delta L/2 * \text{erfc } E_{th}/E)2/t_{PEB}$, where $\Delta L$ is the difference in film thickness between the exposed and unexposed area (also known as the film thickness loss), $t_{PEB}$ is the PEB time, erfc is the error function complement, $E_{th}$ is the exposure dose at which film thickness loss was observed for the first time, and E is the exposure dose. Once the diffusivity has been determined, the diffusion length, DL, can then be calculated with the following equation: $DL=2*(D*t_{PEB})^{1/2}$.

The specific bilayer composition, preparation and process conditions are as follows: the acid detection layer was composed of an acid cleavable polymer A1 (shown below) (5.981% of solution) and tert-butyl 4-hydroxypiperidine-1-carboxylate as a quencher (0.019% of solution) in a 50/50 mix of propylene glycol methyl ether acetate (PGMEA) and methyl 2-hydroxyisobutyrate. The acid source was composed of t-butylacrylate/methylmethacrylate 30/70 copolymer (0.891% of solution) and the PAG (153.40 umol/g of solution) in a 80/20 mixture of 2-methyl-1-butanol and decane. The above solutions were filtered using a PTFE 0.2 μm syringe filter and spin coated onto a silicon wafer coated with a layer of AR™77-840A antireflectant (available from Dow Electronic Materials) using a TEL ATC 8 coater. The acid detection layer was coated first at 1200 Å and prebaked at 110° C. for 60 seconds. After the acid detection layer completed baking, the acid source layer was coated at 300 Å and baked at 90° C. for 60 seconds forming a bilayer system. This stack was then exposed at 193 nm using an ASML 1100 Stepper. The wafer was submitted to a post exposure bake (PEB) of 110° C. for 60 seconds or 120° C. for 60 seconds. During this step, the acid released during exposure in the acid source diffuses into the acid detection layer. Once the PEB is completed, the wafer is developed using 0.26 N aqueous trimethylammonium hydroxide (TMAH). The difference between the film thickness in the unexposed region and the film thickness in the exposed region gives us the total film loss (ΔL). The results are reported in Table 1, where DL=the PAG diffusion length reported in nm.

TABLE 1 polymer A1

| Sample | PAG | Anion structure | DL (nm) at PEB = 110° C. | DL (nm) at PEB = 120° C. |
|---|---|---|---|---|
| Comparative 1 | Triphenylsulfonium perfluotobutanesulfonate | | 67.0 | 155.1 |
| Inventive 1 | PAG-A1 | | 16.0 | 67.0 |
| Inventive 2 | PAG-A2 | | 5.38 | 15.92 |

As can be seen from Table 1, the acid diffusion measurements showed remarkably shorter acid diffusion length for inventive samples PAG-A1 and PAG-A2 compared with the comparative PAG. These results demonstrate the utility of PAGs from the present invention on the manufacturing of highly resolving photoresists with excellent patterning characteristics.

EXAMPLE 5

Lithographic Evaluation

Photoresist preparation: The photoresists were formulated using the components and proportions shown in Table 2. The commercial polymer A2 was used in all examples. Polymer A2 is a pentapolymer that incorporate monomers M1, M2, M3, M4 and M5. The molar ratio of the monomer is M1/M2/M3/M4/M5 is 2/2/3/2/1. The Mw of the polymer was 8000. Note that the PAG (see table), base (t-butyloxycarbonyl-4-hydroxypyridine, TBOC-4HP), and surface leveling agent (surfactant) PF 656, available from Omnova, are each provided below as weight percent based on 100% solids content, with the balance of the solids being the polymer. The solvents used in these formulations are propylene glycol methyl ether acetate (S1) and methyl 2-hydroxyisobutyrate (S2). The final % solids in both examples were 4 wt %. The weight ratio of solvent S1:S2 in the final formulation was 1:1. Photoresist formulation compositions for comparative sample 2 and inventive sample 2 are shown in Table 2 below:

TABLE 2

| | |
|---|---|
| M1 | (structure: ethylcyclopentyl methacrylate) |
| M2 | (structure: adamantyl-substituted methacrylate) |
| M3 | (structure: γ-butyrolactone methacrylate) |
| M4 | (structure: lactone-norbornane methacrylate) |
| M5 | (structure: hydroxyadamantyl methacrylate) |

| Sample | PAG | PAG (wt %) | Base (wt %) | SLA (wt %) |
|---|---|---|---|---|
| Comparative 2 | Triphenylsulfonium perfluotobutane-sulfonate | 9.56 | 1.03 | 0.1 |
| Inventive 4 | PAG-A1 | 13.18 | 1.17 | 0.1 |
| Inventive 5 | PAG-A2 | 13.18 | 1.17 | 0.1 |

Lithographic evaluation: The above photoresists were lithographically processed as follows. The photoresist was spin coated onto a 200 mm silicon wafer having an organic antireflective coating (AR™77, Dow Electronic Materials) and baked at 110° C. for 60 seconds, to form a resist film 100 nm in thickness. The photoresist was exposed with ArF excimer laser (193 nm) through a mask pattern targeting a line and space pattern (L/S pattern) having a line width of 90 nm and a pitch of 180 nm, using an ArF exposure apparatus ASML-1100 (manufactured by ASML), NA (numerical aperture)=0.75 under annular illumination with outer/inner sigma of 0.89/0.64 with focus offset/step 0.10/0.05. Thereafter, post exposure bake (PEB) was conducted at 100° C. for 60 seconds followed by development with 0.26 N aqueous tetramethylammonium hydroxide (TMAH) solution and subsequent water wash. As a result, in each example, a L/S pattern having a line width of 90 nm and a pitch of 180 nm was formed. Mask Error Factor (MEF), Exposure Latitude (EL) were determined by processing the image captured by top-down scanning electron microscopy (SEM) using a Hitachi 9380 CD-SEM, operating at an accelerating voltage of 800 volts (V), probe current of 8.0 picoamperes (pA), using 200 Kx magnification. Exposure latitude (EL) was defined as a difference in exposure energy to print +/−10% of the target diameter normalized by the sizing energy. Mask Error Factor (MEF) was defined as the ratio of CD change on the resolved resist pattern with the relative dimension change on the mask pattern.

The results form the lithographic evaluation of the above photoresist formulations are reported in Table 3. As can be seen, inventive example 4 and 5, which utilize the PAGs PAG-A1 and PAG-A2, respectively, showed improved lithographic performance based on exposure latitude (EL), mask error factor (MEF) and line width roughness (LWR).

TABLE 3

| Sample | Esize (mJ/cm$^2$) | MEF | EL @ 10% of CD Target | LWR 3σ (nm) |
|---|---|---|---|---|
| Comparative 2 | 30.5 | 3.86 | 7.9 | 11.6 |
| Inventive 4 | 53.3 | 3.06 | 9.9 | 11.2 |
| Inventive 5 | 44.2 | 3.1 | 9.8 | 10.8 |

What is claimed is:

1. A photoacid generator having a formula chosen from

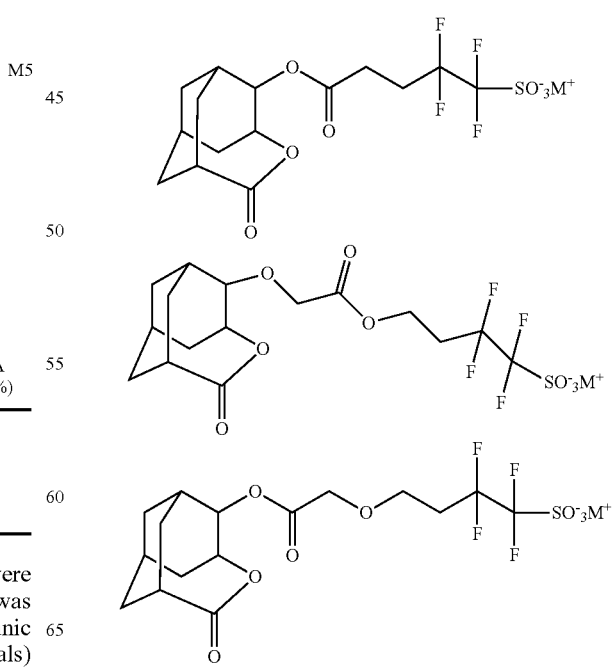

-continued

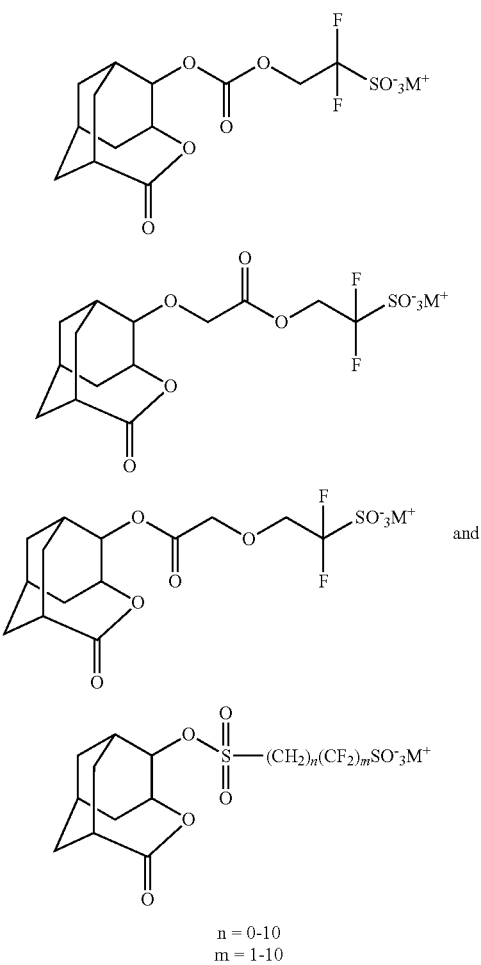

n = 0-10
m = 1-10 wherein M⁺ is a cation.

2. A photoresist composition comprising a polymer and a photoacid generator of claim 1.

3. A method for forming a photoresist relief image on a substrate comprising:
   (a) applying a coating layer of a photoresist composition of claim 2 on a substrate; and
   (b) exposing the photoresist coating layer to patterned activating radiation and developing the exposed photoresist layer to provide a relief image.

4. A photoacid generator of claim 1 having a formula chosen from

-continued n = 0-10
m = 1-10 wherein M⁺ is a cation.

5. A photoresist composition comprising a polymer and a photoacid generator of claim 4.

6. A method for forming a photoresist relief image on a substrate comprising:
   (a) applying a coating layer of a photoresist composition of claim 5 on a substrate; and
   (b) exposing the photoresist coating layer to patterned activating radiation and developing the exposed photoresist layer to provide a relief image.

7. A photoacid generator of claim 1 having a formula chosen from

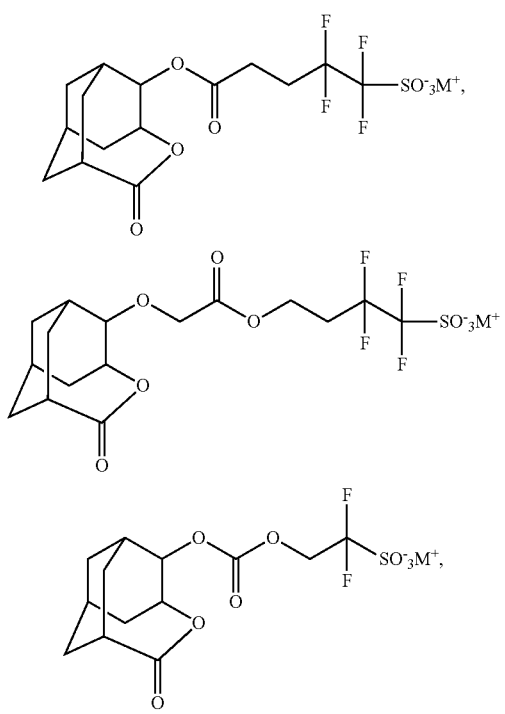

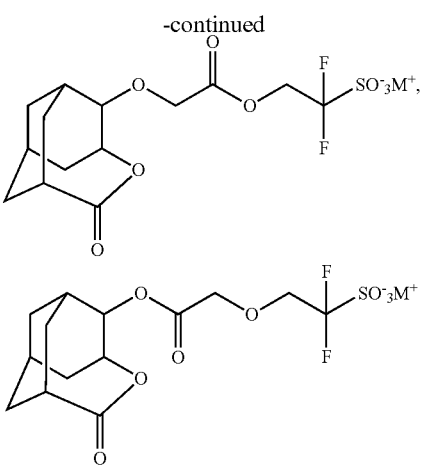

wherein M⁺ is a cation.

8. A photoresist composition comprising a polymer and a photoacid generator of claim 7.

9. A method for forming a photoresist relief image on a substrate comprising:
(a) applying a coating layer of a photoresist composition of claim 8 on a substrate; and
(b) exposing the photoresist coating layer to patterned activating radiation and developing the exposed photoresist layer to provide a relief image.

* * * * *